United States Patent [19]

Bagley et al.

[11] Patent Number: 4,912,109

[45] Date of Patent: Mar. 27, 1990

[54] N-HETEROCYCLIC-N-(4-PIPERIDINYL) AMIDES AND PHARMACEUTICAL COMPOSITIONS AND METHODS EMPLOYING SUCH COMPOUNDS

[75] Inventors: Jerome R. Bagley, North Plainfield; H. Kenneth Spencer, Chatham, both of N.J.

[73] Assignee: BOC, Inc., New Providence, N.J.

[21] Appl. No.: 282,092

[22] Filed: Dec. 9, 1988

Related U.S. Application Data

[63] Continuation-in-part of Ser. No. 9,857, Feb. 2, 1987, Pat. No. 4,791,112.

[51] Int. Cl.$^4$ ................. A61K 31/435; A61K 31/495; C07D 241/02; C07D 213/02

[52] U.S. Cl. ..................................... 514/252; 514/256; 514/269; 514/272; 514/274; 514/275; 514/318; 544/336; 544/408; 544/409; 544/332; 544/311; 544/312; 544/316; 544/317; 544/319; 544/320; 544/321; 544/327; 544/329; 544/405; 546/193; 546/194

[58] Field of Search ............... 544/336, 408, 409, 405; 514/252

[56] References Cited

U.S. PATENT DOCUMENTS 4,157,393  6/1979  Sanczuk et al. ..................... 424/251
4,546,105 10/1985  Effland et al. ....................... 514/334
4,584,303  4/1986  Huang et al. ........................ 514/326
4,788,198 11/1988  Grozinger et al. .................. 544/408

OTHER PUBLICATIONS

Studies on Potent Analgesics, Youcheng et al., 3/81, 12 page Article (Acta Pharmaceutica Sinica) vol. XVI, No. 3. S. Grossmann et al., Pyridin–Analoga Des Fentanyls, 1978, 6 page Article, (Arch. Pharm. Weinheim). Janssens et al., New Antihistiminic N–Heterocyclic 4–Piperidiamines 1985, 5 pages (J. Med. Chem) vol. 28, No. 12, pp. 1925–1947.
Youcheng et al., Structural Modification of 4–N–Propionyl Group, etc. 1983, 7 pages (Yaoxue Xuebo 18(8) 591–6.

Primary Examiner—Mary C. Lee
Assistant Examiner—J. Richter
Attorney, Agent, or Firm—R. Hain Swope; Larry R. Cassett

[57] ABSTRACT

This invention pertains to novel substituted N-heterocyclic-N-(4-piperidinyl)amides useful as analgesics and antagonists of opiods, wherein the compounds have the general formula:

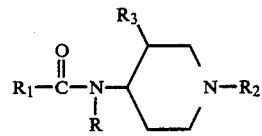

including optically active isomeric forms, and the pharmaceutically acceptable acid addition salts thereof, wherein:

R is a substituted or unsubstituted unsaturated heterocyclic ring system having 5 to 6 cyclic member atoms containing at least one nitrogen atom, and is preferably selected from the group consisting of pyridinyl, pyrimidinyl, and pyrazinyl;

$R_1$ is selected from the group consisting of unsubstituted or substituted heterocyclic ring systems having 5 cyclic member atoms, lower cyclic alkyl ring systems, lower-alkyl and lower-alkoxy lower-alkyl, and is preferably selected from the group consisting of furanyl lower-alkyl, thienyl lower-alkyl, pyrrolyl lower-alkyl, lower-alkyl, lower-cycloalkyl, and lower-alkoxy lower-alkyl of 2 to 6 carbons;

$R_2$ is a cyclic ring system lower-alkyl having 5 to 6 cyclic member atoms, and is preferably selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl which may be substituted in the 4-position with a group selected from lower-alkyl; and $R_3$ is selected from the group consisting of hydrogen and methyl.

21 Claims, No Drawings

N-HETEROCYCLIC-N-(4-PIPERIDINYL) AMIDES AND PHARMACEUTICAL COMPOSITIONS AND METHODS EMPLOYING SUCH COMPOUNDS

This application is a continuation-in-part of our co-pending U.S. application Ser. No. 009,857 filed Feb. 2, 1987 now U.S. Pat. No. 4,791,112, issued Dec. 13, 1988.

The present invention relates to substituted N-heterocyclic-N-(4-piperidinyl)amides, and pharmaceutical compositions and methods employing such compounds.

BACKGROUND OF THE INVENTION

Antagonists are substances that tend to nullify the action of another substance (the agonist). Antagonists of narcotics are believed to function by binding competitively to the opioid receptor, thereby preventing occupation of the receptor by the (therapeutic) agonist. At least four types of opioid receptors have been identified in the central nervous system—mu, kappa, sigma, and delta. The affinity of a particular antagonist for each receptor may not be equal. In general, antagonists have a greater affinity for the mu receptor. Antagonist compounds may act centrally or peripherally, may act at specific opiate receptor sites or through a non-specific analeptic mechanism or through a neurotransmitter system.

A number of patents disclose certain N-heterocyclic-N-(4-piperidinyl)amides having therapeutic activity. For example, U.S. Pat. No. 4,546,105, issued to Effland et al. and assigned to Hoechst-Roussel Pharmaceuticals Inc., discloses N-pyrrolyl-N-(4-piperidinyl)amine and amide compounds useful as analgesics. An article entitled "Synthesis and Analgesic Activity of Derivatives of Fentanyl" by Zhu Youcheng et al., printed in *Acta Pharmaceutica Sinica*, Vol. XVI, No. 3, pp. 199–209 Mar. 1981, discloses the synthesis of substituted N-aryl-N-(4-piperidinyl)amide compounds which possess morphine-like activities. Sigmar Grossman et al., in *Arch. Pharm.* (Weinheim) 311, pp. 1010–1015 (1978), disclose the preparation of substituted N-pyridine analogues of fentanyl which possess analgesic activity. Frans Janssens et al., in *Journal of Medicinal Chemistry*, Vol. 28, No. 12, pp. 1925–1933, 1934–1943, 1943–1947 (1985), disclose the synthesis of masked N-substituted-N-(4-piperidinyl)amides which possess antihistaminic properties.

Naloxone, also known as 4,5-epoxy-3,14-dihydroxy-17-(2-propenyl)morphinan-6-one, has gained widespread use in anesthesia as an antagonist for opioid widespread use in anesthesia an antagonist for opioid induced respiratory depression and sedation, (Editorial, *British Journal of Anesthesia*, Vol. 57, No. 6, pp. 547–549 Jun. 1985. Naloxone is mainly used to terminate undesirable opioid effects during the immediate post operative period.

The use of naloxone as an anesthesia antagonist has disadvantages. These disadvantages include, for example, undesirable side effects such as ventricular dysrhythmia, hypertension and pulmonary edema following intravenous administration of the drug. Naloxone also tends to reverse or antagonize the desirable analgesic effects of opioids.

Accordingly there is a need for a safe drug which will antagonize the undesirable effects of opioids such as respiratory and cardiac depression without antagonizing the desirable effects such as analgesia and anesthesia. The present invention provides such compounds, methods by which these compounds may be prepared, and pharmaceutical compositions and methods employing such compounds.

SUMMARY OF THE INVENTION

This invention pertains to novel substituted N-heterocyclic-N-(4-piperidinyl)amides useful as analgesics and antagonists of opioids, and methods of administering analgesia and reversing the undesirable effects of opioids, which comprises the systemic administration to mammals of such compounds, and pharmaceutical compositions containing such compounds, wherein the compounds have the general formula:

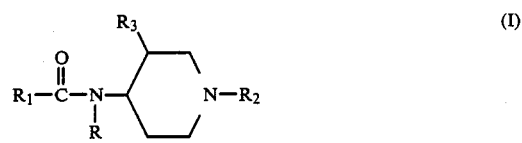

including optically active isomeric forms, and the pharmaceutically acceptable acid addition salts thereof, wherein:

R is an unsubstituted or substituted unsaturated heterocyclic ring system having 5 to 6 cyclic member atoms containing at least one nitrogen atom, and is preferably selected from the group consisting of pyridinyl, pyrimidinyl, and pyrazinyl;

$R_1$ is selected from the group consisting of unsubstituted or substituted heterocyclic ring systems having 5 cyclic member atoms, lower-cycloalkyl ring systems, lower-alkyl and lower-alkoxy lower-alkyl, and is preferably selected from the group consisting of furanyl lower-alkyl, thienyl lower-alkyl, pyrrolyl lower-alkyl, lower-alkyl, lower-cycloalkyl, and lower-alkoxy lower-alkyl of 2 to 6 carbons;

$R_2$ is a cyclic ring system lower-alkyl having 5 to 6 cyclic member atoms, and is preferably selected from the group consisting of phenyl lower-alkyl, thienyl lower-alkyl, thienyl hydroxy lower-alkyl; pyrazoyl lower-alkyl, and (4,5-dihydro-5-oxo-1H-tetrazol-1-yl) lower-alkyl which may be substituted in the 4-position with a group selected from lower-alkyl; and $R_3$ is selected from the group consisting of hydrogen and methyl.

DETAILED DESCRIPTION OF THE INVENTION

The compounds of the present invention possess very desirable analgesic agonist-antagonist activities. Certain of the compounds of the present invention (agonists) have central nervous system depressant properties which include analgesia, hypnosis, sedation, muscle relaxation, increased pain threshold, and barbiturate and/or general anesthetic potentiation. Many of the compounds provide highly potent analgesia with a short duration of action. These properties are highly desirable in circumstances where acute severe pain must be eliminated over a short period of time, such as in anesthesiology. The preferred agonist compounds of the present invention have comparatively low respiratory depressive and/or cardiovascular depressive activity. At high dosage levels, the agonist compounds produce sedation which causes loss of righting reflex, hypnosis and loss of consciousness.

Certain of the compounds of the present invention (antagonists) have been found to cause reversal of at least some of the activities of analgesics and anesthetics. The preferred antagonist compounds of the present invention selectively reverse the respiratory depressive and/or cardiovascular depressive activity of narcotic or opiate analgesics without reversing the analgesia activity at that dose level. Antagonist compounds of the present invention are useful for control of post operative pain when respiratory depressive and/or cardiovascular depressive activity, but not analgesia activity, must be reversed.

The compounds of the present invention may be used together with a pharmaceutically acceptable carrier to provide pharmaceutical compositions and can be administered to mammals such as man in amounts sufficient to provide analgesic effects or to reverse certain analgesic effects.

As set out above, the analgesic agonistantagonist compounds of the present invention have the general formula:

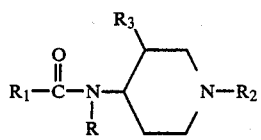

including optically active isomeric forms, and the pharmaceutically acceptable acid addition salts thereof, and wherein R, $R_1$, $R_2$ and $R_3$ are defined as set forth below:

Group R in Formula I above is an unsaturated heterocyclic ring system having 5 to 6 cyclic member atoms containing at least one nitrogen atom. The preferred heterocyclic ring systems are selected from the group consisting of pyridinyl, pyrimidinyl, and pyrazinyl. The pyridinyl group is preferably attached to nitrogen at the 2 or 3 position of the pyridinyl ring. The pyrimidinyl group is preferably attached to nitrogen at the 2 position of the pyrimidinyl ring.

The heterocyclic ring system groups may be either unsubstituted or substituted, wherein the substituents are independently selected from the group consisting of halogen, lower-alkyl, lower-alkoxy, halogenated lower-alkyl, lower-alkylthio, oxygen, and combinations thereof. The preferred substituents are chloro and methyl. The preferred substituted heterocyclic ring systems are 2-methyl-6-pyridinyl and 4-methyl-2-pyridinyl.

Group $R_1$ in Formula I above is selected from the group consisting of heterocyclic ring systems having 5 cyclic member atoms, lower-cycloalkyl ring systems, lower-alkyl and lower-alkoxy lower-alkyl. In a preferred embodiment, the $R_1$ group is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons. The furanyl or thienyl group can be attached to the carbonyl carbon atom at the 2 or 3 position of the thienyl or furanyl ring.

The $R_1$ group may be either unsubstituted or substituted, wherein the substituents are independently selected from the group consisting of halogen, lower-alkyl, lower-alkoxy, halogenated lower-alkyl, lower-alkylthio, oxygen, and combinations thereof. The preferred substituents are bromo and methyl. In a preferred embodiment, the $R_1$ groups are 2,5-dimethyl-3-furanyl, 2-bromo-5-furanyl, 1-methyl-2-pyrrolyl, cyclopropanyl, and methoxymethyl.

Group $R_2$ in Formula I above is an unsaturated cyclic ring system lower-alkyl having 5 to 6 cyclic member atoms. The preferred cyclic ring systems are selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl.

The $R_2$ group may be either unsubstituted or substituted, wherein the substituents are independently selected from the group consisting of halogen, lower-alkyl, lower-alkoxy, halogenated lower-alkyl, lower-alkylthio, oxygen, and combinations thereof. The preferred substituents are methyl, ethyl and hydroxy. In a preferred embodiment, the $R_2$ groups are phenylmethyl, phenylethyl, 2-(2-thienyl)ethyl, 2-(3-thienyl)ethyl, 2-(2-thienyl)-2-hydroxyethyl, 2-(2-thienyl)-1-methyl-2-hydroxyethyl, 2-(4-ethyl-4,5-dihydro-5-oxo-1H-tetrazol-1-yl)ethyl, and 2-(1-pyrazolyl)ethyl.

Group $R_3$ in Formula I above is selected from the group consisting of hydrogen and methyl.

A preferred class of compounds within the scope of the present invention has the general formula:

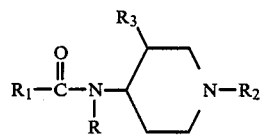

including optically active isomeric forms, and the pharmaceutically acceptable acid addition salts thereof, wherein:

R is selected from the group consisting of pyrimidinyl, pyridinyl, and pyrazinyl. The pyridinyl group is preferably attached to nitrogen at the 2 or 3 position of the pyridinyl ring. The pyrimidinyl group is preferably attached to nitrogen at the 2 position of the pyrimidinyl ring. The R groups may be unsubstituted or substituted with the substituents independently selected from the group consisting of halogen, lower-alkyl, lower-alkoxy, halogenated lower-alkyl, lower-alkylthio, oxygen, and combinations thereof. The preferred substituents are chloro and methyl. The preferred substituted heterocyclic ring systems are 2-methyl-6-pyridinyl and 4-methyl-2-pyridinyl.

$R_1$ is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons. The furanyl or thienyl group can be attached to the carbonyl carbon atom at the 2 or 3 position of the thienyl or furanyl ring. The $R_1$ group may be either unsubstituted or substituted with the substituents independently selected from the group consisting of halogen, lower-alkyl, lower-alkoxy, halogenated lower-alkyl, lower-alkylthio, oxygen, and combinations thereof. The preferred substituents are bromo and methyl. In a preferred embodiment, the $R_1$ groups are 2,5-dimethyl-3-furanyl, 2-bromo-5-furanyl, 1-methyl-2-pyrrolyl, cyclopropanyl, and methoxymethyl.

$R_2$ is selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl. The $R_2$ group may be either unsubstituted or substituted with the substituents selected independently from the group consisting of halogen, lower-alkyl, lower-alkoxy, halogenated lower-alkyl, lower-alkylthio, oxygen, and combinations thereof. The preferred substituents are methyl, ethyl and hydroxy. In a preferred embodiment, the R₂ groups are phenylmethyl, phenylethyl, 2-(2-thienyl)ethyl, 2-(3-thienyl)ethyl, 2-(2thienyl)-2-hydroxyethyl, 2-(2-thienyl)-1-methyl-2-hydroxyethyl, 2-(4-ethyl-4,5-dihydro-5-oxo-1H-tetrazol-1-yl)ethyl, and 2-(1-pyrazolyl)ethyl.

$R_3$ is hydrogen.

Another preferred class of compounds within the scope of the present invention has the general formula:

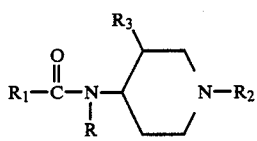
(I)

including optically active isomeric forms, and the pharmaceutically acceptable acid addition salts thereof, wherein:

R is selected from the group consisting of pyrimidinyl, pyridinyl, and pyrazinyl. The pyridinyl group is preferably attached to nitrogen at the 2 or 3 position of the pyridinyl ring. The pyrimidinyl group is preferably attached to nitrogen at the 2 position of the pyrimidinyl ring. The R groups may be unsubstituted or substituted with the substituents independently selected from the group consisting of halogen, lower-alkyl, lower-alkoxy, halogenated lower-alkyl, lower-alkylthio, oxygen, and combinations thereof. The preferred substituents are chloro and methyl. The preferred substituted heterocyclic ring systems are 2-methyl-6-pyridinyl and 4-methyl-2-pyridinyl.

$R_1$ is selected from the group consisting of furanyl lower-alkyl, thienyl, thienyl lower-alkyl, pyrrolyl, pyrrolyl lower-alkyl, and lower-alkyl and lower-cycloalkyl of 2 to 6 carbons. The furanyl or thienyl group can be attached to the carbonyl carbon atom at the 2 or 3 position of the thienyl or furanyl ring. The $R_1$ group may be either unsubstituted or substituted with the substituents independently selected from the group consisting of halogen, lower-alkyl, lower-alkoxy, halogenated lower-alkyl, lower-alkylthio, oxygen, and combinations thereof. The preferred substituents are bromo and methyl. In a preferred embodiment, the $R_1$ groups are 2,5-dimethyl-3-furanyl, 2-bromo-5-furanyl, 1-methyl-2-pyrrolyl, cyclopropanyl, and methoxymethyl.

$R_2$ is selected from the group consisting of thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl. The $R_2$ group may be either unsubstituted or substituted with the substituents selected independently from the group consisting of halogen, lower-alkyl, lower-alkoxy, halogenated lower-alkyl, lower-alkylthio, oxygen, and combinations thereof. The preferred substituents are methyl, ethyl and hydroxy. In a preferred embodiment, the R₂ groups are 2-(2-thienyl)ethyl, 2-(3-thienyl)ethyl, 2-(2-thienyl)-2-hydroxyethyl, 2-(2-thienyl)-1-methyl-2-hydroxyethyl, 2-(4-ethyl-4,5-dihydro-5-oxo-1H-tetrazol-1-yl)ethyl, and 2-(1-pyrazolyl)ethyl.

$R_3$ is hydrogen.

Another preferred class of compounds within the scope of the present invention has the general formula:

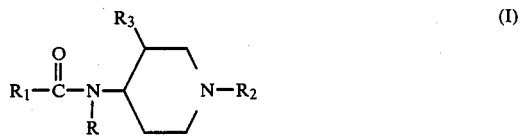
(I)

including optically active isomeric forms, and the pharmaceutically acceptable acid addition salts thereof, wherein:

R is selected from the group consisting of pyrimidinyl, pyridinyl, and pyrazinyl. The pyridinyl group is preferably attached to nitrogen at the 2 or 3 position of the pyridinyl ring. The pyrimidinyl group is preferably attached to nitrogen at the 2 position of the pyrimidinyl ring. The R groups may be unsubstituted or substituted with the substituents independently selected from the group consisting of halogen, lower-alkyl, lower-alkoxy, halogenated lower-alkyl, lower-alkylthio, oxygen, and combinations thereof. The preferred substituents are chloro and methyl. The preferred substituted heterocyclic ring systems are 2-methyl-6-pyridinyl and 4-methyl-2-pyridinyl.

$R_1$ is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons. The furanyl or thienyl group can be attached to the carbonyl carbon atom at the 2 or 3 position of the thienyl or furanyl ring. The $R_1$ group may be either unsubstituted or substituted with the substituents independently selected from the group consisting of halogen, lower-alkyl, lower-alkoxy, halogenated lower-alkyl, lower-alkylthio, oxygen, and combinations thereof. The preferred substituents are bromo and methyl. In a preferred embodiment, the $R_1$ groups are 2,5-dimethyl-3-furanyl, 2-bromo-5-furanyl, 1-methyl-2-pyrrolyl, cyclopropanyl, and methoxymethyl.

$R_2$ is selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl. The $R_2$ group may be either unsubstituted or substituted with the substituents selected independently from the group consisting of halogen, lower-alkyl, lower-alkoxy, halogenated lower-alkyl, lower-alkylthio, oxygen, and combinations thereof. The preferred substituents are methyl, ethyl and hydroxy. In a preferred embodiment, the R₂ groups are phenylmethyl, phenylethyl, 2-(2-thienyl)ethyl, 2-(3-thienyl)ethyl, 2-(2-thienyl)-2-hydroxyethyl, 2-(2-thienyl)-1-methyl-2-hydroxyethyl, 2-(4-ethyl-4,5-dihydro-5-oxo-1-H-tetrazol-1-yl)ethyl, and 2-(1-pyrazolyl)ethyl.

$R_3$ is methyl.

·The term lower-alkyl groups, as used herein, means branched or unbranched alkyl groups containing from 1 to 7 carbon atoms. The term lower-alkoxy groups, as used herein, means branched or unbranched alkoxy groups containing from 1 to 7 carbon atoms. The term lower-cycloalkyl groups, as used herein, means cyclic alkyl groups containing from 3 to 6 carbon atoms. Preferred heterocyclic groups include from 6 to 12 carbon atoms and can include the substituents discussed above in connection with heterocyclic groups.

The compounds of the present invention which have at least one asymmetric carbon atom can exist in optically active isomeric forms. For example, in compounds in which $R_2$ is a 2-phenyl-1-propyl or 1-phenyl-2-propyl group, etc., the carbon adjacent to the piperidinyl nitrogen is an asymmetric carbon atom and such compounds can therefore exist in optical active isomeric (enantiomeric) forms. Such isomeric forms can be isolated from the racemic mixtures by techniques known to those skilled in the art.

The compounds of the present invention which have a methyl group as the $R_3$ group exist in cis or trans form. Such compounds can be used as a mixture of such forms but many times one form is more active than the other or one form has other desirable characteristics. Thus many times it is desirable to resolve the cis/trans mixture. This resolution can be accomplished by techniques conventional in the art for such purpose, e.g., chromatographic techniques such as column chromatography or high pressure liquid chromatography or simple recrystallization techniques.

The compounds of the present invention can be prepared by various methods. In general, the desired compounds having Formula I above can be prepared by reacting a compound having the formula:

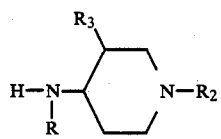

with a compound having the formula:

$R_1$-CO-X or $(R_1CO)_2O$ or by reacting a compound having the formula:

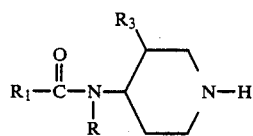

with a compound having the formula:

$R_2X$ wherein the substituent groups R, $R_1$, $R_2$ and $R_3$ have the definitions set out above, and X represents halide or its reactive equivalnet. Examples of halide reactive equivalents are toluene sulfonate, phenyl sulfonate and methyl sulfonate and the like.

In the first reaction, when the $R_2$ group is phenylmethyl (benzyl), the phenylmethyl group can be cleaved by reaction with 1-chloroethyl chloroformate followed by hydrolysis with methanol, see R. A. Olofson et al., *J. Org. Chem.*, 49, pp. 2081–2082 (1984), and replaced with other $R_2$ groups such as furanyl lower-alkyl, thienyl lower-alkyl, pyrazoyl lower-alkyl and the like.

Several convenient routes for the preparation of the compounds of the invention begin with known piperidone starting materials as shown below:

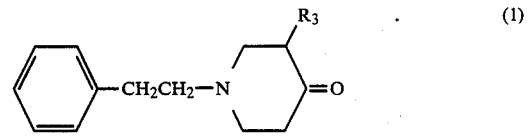

(1)

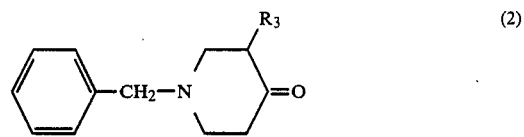

(2)

The compound 1-(2-phenylethyl)-4-piperidone (1), when $R_3$=H, or 1-(2-phenylethyl)-3-methyl-4-piperidone (1), when $R_3$=CH$_3$, can be prepared according to the procedure published by A. H. Becket, A. F. Casey and G. Kirk, *J. Med Pharm. Chem.*, Vol. 1, p. 37 (1959). The compound 1-phenylmethyl-4-piperidone (2), when $R_3$=H, or 1-phenylmethyl-3-methyl-4-piperidone (2), when $R_3$=CH$_3$, can be prepared in an analogous manner by the procedure described by C. R. Ganellin and R. G. Spickch, *J. Med. Chem.*, Vol. 8, p. 619 (1965) or P. M. Carabateas and L. Grumbach, *J. Med. Pharm. Chem.*, Vol. 5, p. 913 (1962).

In one example of a method for preparing the compounds of the present invention, 1-phenylmethyl or 1 (2-phenylethyl)-4-piperidone is reacted with an unsubstituted or substituted heterocyclic amine to form a Schiff base. The Schiff base is then reduced, for example, with sodium borohydride to yield the unsubstituted or substituted 1-phenylmethyl or 1-(2-phenylethyl)-4-(N-aminoheterocycle)-piperidine compound. See for example, S. Grossman et al., *Arch. Pharm.* (Weinheim) 311, p. 1010 (1978). The following reaction scheme, wherein R is a heterocyclic group within the definition of the present invention, illustrates such a method:

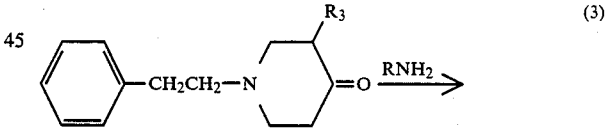

(3)

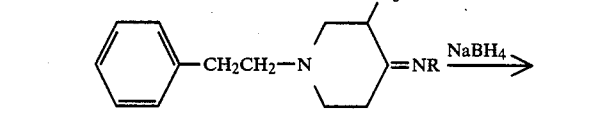

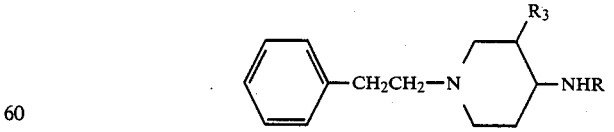

When the $R_3$ group is hydrogen, compound (3) can be reacted with an appropriate acid halide (e.g., $R_1COCl$) or an anhydride (e.g., $(R_1CO)_2O$) to introduce the desired $R_1$-carbonyl group on the nitrogen atom and thereby obtain compound (I) of the present invention, according to the reaction scheme shown below:

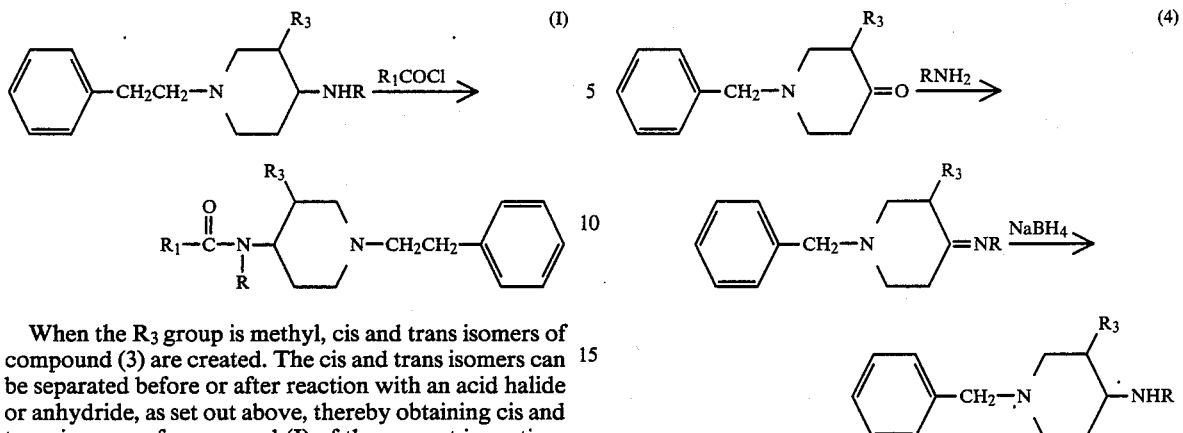

When the R₃ group is methyl, cis and trans isomers of compound (3) are created. The cis and trans isomers can be separated before or after reaction with an acid halide or anhydride, as set out above, thereby obtaining cis and trans isomers of compound (I) of the present invention. The separation of the cis/trans isomers can be carried out according to the following reaction scheme:

As set out above, when the R₃ group is methyl, com-

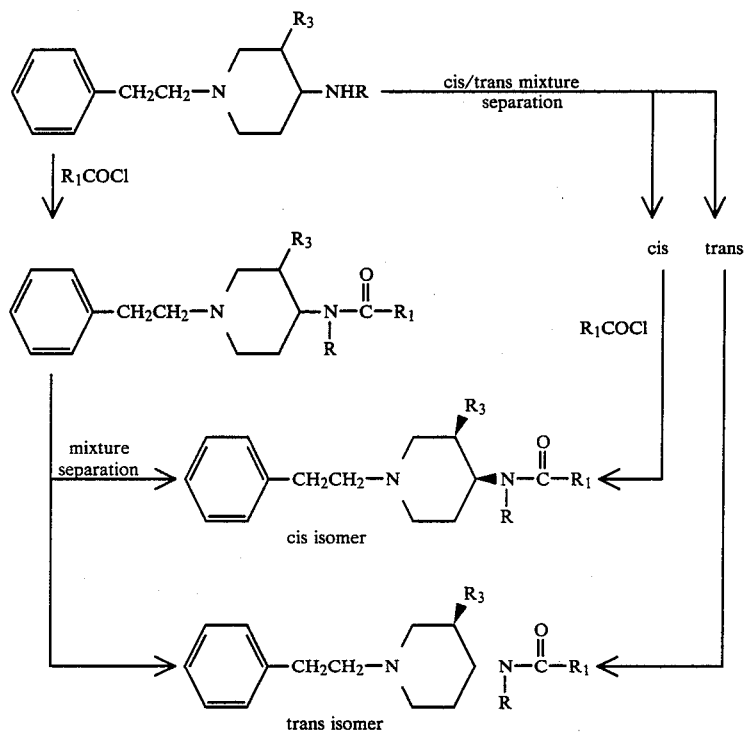

When the desired R₂ substituent group is not phenylethyl, one procedure for preparing compounds of the present invention with different R₂ groups is to remove the phenylmethyl group by reaction with 1-chloroethyl chloroformate in compound (2) above and replace it with a desired R₂ group. For example, compounds of the invention can be prepared according to the following scheme:

pound (4) is a mixture of cis and trans isomers which can be separated prior to the next step. When the R₃ group is hydrogen, no preliminary cis-trans isomer separation is necessary. After any such cis/trans separation, compound (4) can be reacted with 1-chloroethyl chloroformate according to the following reaction scheme to remove the phenylmethyl group and prepare piperidinyl intermediate (5):

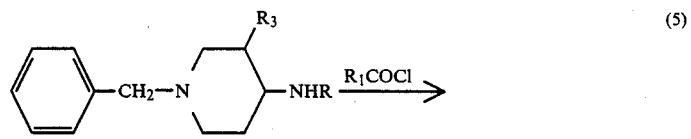

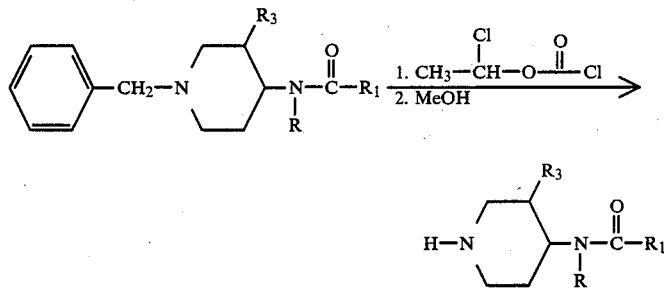

The desired $R_2$ substituent group can then be introduced by reacting compound (5) with an appropriately reactive molecule $R_2$-X, wherein X is halogen, such as chlorine, bromine, or iodine, or its reactive equivalent, to obtain compound (I) of the present invention according to the reaction scheme illustrated below:

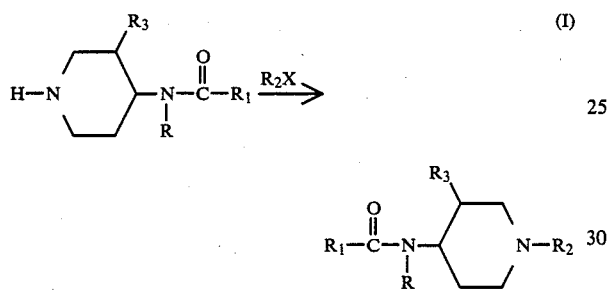

The reaction of $R_2$-X with a piperdinyl intermediate such as compound (5) can be conducted in an inert organic solvent such as, for example, an aromatic hydrocarbon, a ketone such as 4-methyl-2-pentanone and the like, an ether such as 1,4-dioxane, diethylether, tetrahydofuran, 1,2-dimethoxyethane and the like, or N,N-dimethylformamide. The addition of an appropriate base, such as an alkali metal carbonate, may be utilized to neutralize the acid generated during the reaction. The addition of an iodide salt, such as an alkali metal iodide, may be appropriate. The temperature of the reaction mixture may be raised to increase the rate of reaction when appropriate.

In an alternative procedure, the phenylmethyl group can first be removed by reaction with 1-chloroethyl chloroformate prior to separation of the cis/trans isomers of compound (4) to obtain compound (I) of the present invention with the $R_1$ and $R_2$ groups introduced according to one of the two schemes shown below:

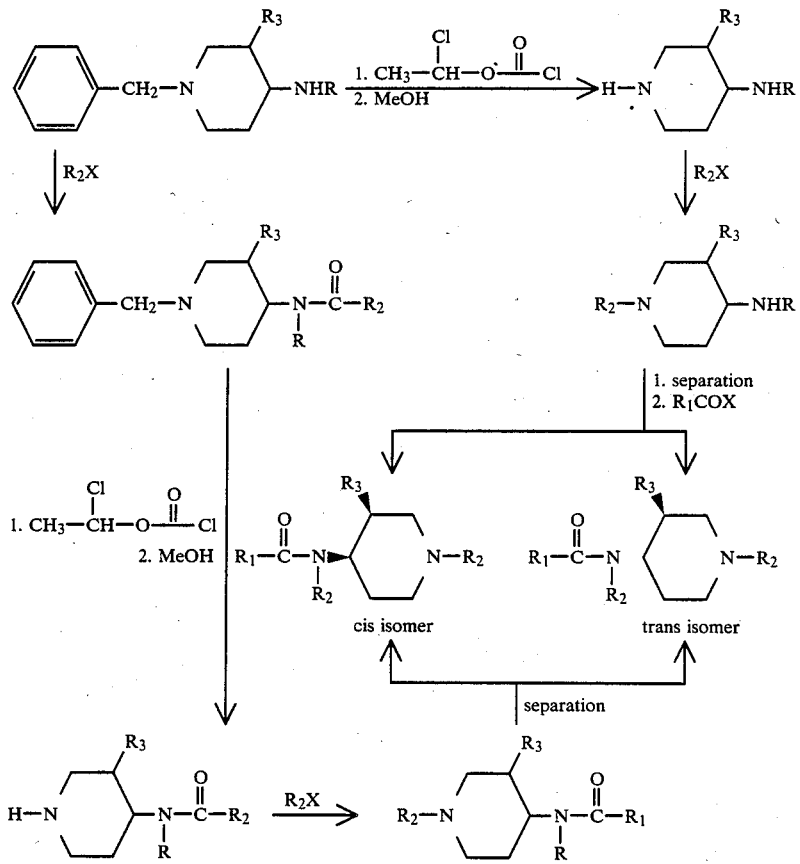

In a second example of a method for preparing the compounds of the present invention, an intermediate such as 1-(phenylethyl)-4-piperidineamine (6) is utilized. In this method, the primary amine is reacted with a heterocycle group R to form a secondary amine precursor (7). The secondary amine is then acylated. See, for example, Y. Zhu et al., *Acta Pharm. Sinica,* 16, p. 199 (1981). The following reaction scheme, wherein R is a heterocyclic group within the definition of the present invention, illustrates such a method to make compound (I) of the present invention.

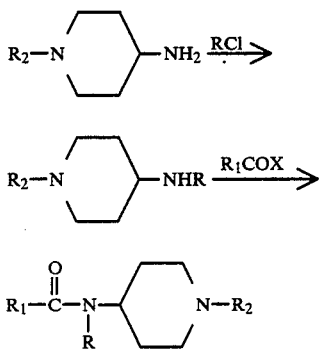

In a third example of a method for preparing the compounds of the present invention, the same intermediate, such as 1-(phenylethyl)-4-piperidineamine (6), is utilized. In this method, the primary amine is reacted with an oxo-derivative of the heterocycle group R to form a secondary amine precursor (8). The oxo-intermediate is reduced prior to acylation. See, for example, Langhein et al., *Offenlegungschrift,* 234, p. 1965 (1975); Chem. Abstr. 82, 156121w (1975). The following reaction scheme, wherein R is a heterocyclic group within the definition of the present invention, illustrates such a method to make compound (I) of the present invention.

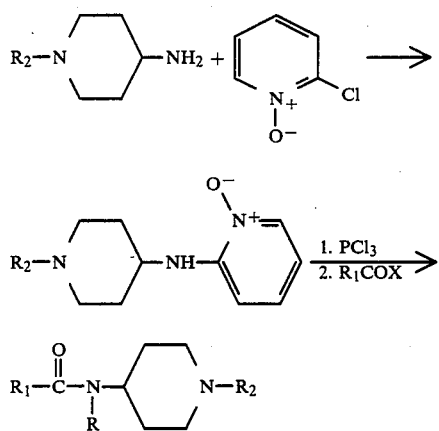

The compounds of the present invention while effective in the form of the free base may be formulated and administered in the form of the therapeutically or pharmaceutically acceptable acid addition salts for purposes of stability, convenience of crystallization, increased solubility and the like. These acid addition salts include inorganic acid salts such as hydrochloric, hydrobromic, sulfuric, nitric, phosphoric, perchloric acid salts and the like; and organic acid salts such as acetic, trifluoroacetic, propionic, oxalic, hydroxyacetic, methoxyacetic, 2-hydroxypropanoic, 2-oxopropanoic, propanedioic, 2-hydroxy-butanedioic, benzoic, 2-hydroxybenzoic, 4-amino-2-hydroxy-benzoic, 3-phenyl-2-propenoic, alpha-hydroxybenzeneacetic, methanesulfonic, ethanesulfonic, benzenesulfonic, toluene-sulfonic, cyclohexanesulfamic, succinic, tartaric, citric, maleic, fumaric acid salts and the like. The preferred acid addition salts are chloride, oxalate and citrate. These acid addition salts can be prepared by conventional methods, such as by treatment of the free base of the inventive compound with the appropriate acid.

The compounds of the present invention, prepared in the free base form, can be combined with a pharmaceutically acceptable carrier to provide a pharmaceutical composition. Suitable carriers for the free bases include propylene glycol-alcohol-water, isotonic water, sterile water for injection (USP), emulphor TM -alcohol-water, cremophor-EL TM or other suitable carriers known to those skilled in the art.

The compounds of the present invention, prepared in the pharmaceutically acceptable acid addition salt form, can also be combined with a pharmaceutically acceptable carrier to provide a pharmaceutical composition. Suitable carriers for the acid addition salts include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to provide the desired analgesic therapeutic effect or to reverse the actions of an opiate analgesic. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 0.00005 mg/kg, which the practitioner may titrate to the desired effect.

The compounds of the present invention can be administered parenterally, in the form of sterile solutions or suspensions, such as intravenously, intramuscularly or subcutaneously in the carriers previously described. The compounds may also be administered orally, in the form of pills, tablets, capsules, troches, and the like, as well as sublingually, rectally, or transcutaneously with a suitable pharmaceutically acceptable carrier for that particular mode of administration as is conventional in the art.

For parental therapeutic administration, the compounds of the present invention may be incorporated into a sterile solution or suspension. These preparations should contain at least about 0.1% of the inventive compound, by weight, but this amount may be varied to between about 0.1 and about 50% of the inventive compound, by weight of the parental composition. The exact amount of the inventive compound present in such compositions is such that a suitable dosage level will be obtained. Preferred compositions and preparations according to the present invention are prepared so that a paranteral dosage unit contains from between about 5.0 to about 100 milligrams of the inventive compound.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parental preparations may be enclosed in ampules, disposable syringes, or multiple dose vials made of glass or plastic.

The compounds of the present invention can also be administered orally. For oral therapeutic administration, the compounds may be incorporated with excipients and used in the form of tablets, capsules, elixirs, suspensions, syrups, wafers, chewing gums and the like. These preparations should contain at least about 4% of the inventive compound, by weight, but this amount may be varied depending upon the particular dosage form from between about 4% to about 70% of the inventive compound, by weight of the oral composition. The exact amount of the compound present in the composition is such that a suitable dosage will be obtained. Preferred compositions and preparations according to the present invention are prepared so that an oral dosage unit form contains from between about 5 to about 300 milligrams of the inventive compound.

The tablets, pills, capsules, troches and the like may also contain the following adjuvants: a binder, such as microcrystalline cellulose, gum tragacanth or gelatine; an excipient, such as starch or lactose; a disintegrating agent, such as alginic acid, Primogel, corn starch and the like; a lubricating agent, such as magnesium stearate or Sterotex; a gliding agent, such as colloidal silicon dioxide; a sweetening agent, such as sucrose or saccharin; and a flavoring agent, such as peppermint, methyl salicylate or orange flavoring. When the dosage form is a capsule, it may additionally contain a liquid carrier such as a fatty oil. Other dosage unit forms may contain other materials which modify the physical form of the dosage unit, such as enteric coatings. Thus tablets or pills may be coated with sugar, shellac, or other enteric coating agents. A syrup may contain, in addition to the above adjuvants, sucrose as a sweetening agent, preservatives, dyes, coloring agents and flavoring agents.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is further illustrated by the following examples which are presented for purposes of demonstrating, but not limiting, the preparation of the compounds and compositions of this invention.

EXAMPLE I

This Example illustrates the preparation of an oxime (Schiff base) intermediate.

A quantity of 50 g (0.246 mol) of 1-(2-phenylethyl)-4-piperidone (recrystallized from hexane prior to use) was dissolved with heating in 200 ml of ethanol. This ethanolic solution was added to a warm solution of 34.2 g (0.492 mol) of hydroxylamine hydrochloride in 200 ml of deionized water. An additional 500 ml of water was added to the solution to dissolve the 1-(2-phenylethyl)-4-piperidone oxime hydrochloride which began to precipitate. Solid sodium bicarbonate (41.3 g, 0.492 mol) was added to the reaction solution in portions. The mixture was heated to the boiling point and then allowed to cool to room temperature. Ice was added to the mixture which was then stirred overnight. The solid product was filtered off, washed with water (5×200 ml), and then dried under vacuum. The crude 1-(2-phenylethyl)-4-piperidine oxime (52 g, 97%, mp. 132°–133° C.) was sufficiently pure for direct use in the next reaction. An analytically pure sample of oxime (mp. 132.5°–134.5° C.) was obtained by recrystallization of the material from 95% ethanol.

|   | Calcd. | Found |
|---|--------|-------|
| C | 71.52  | 71.76 |
| H | 8.31   | 8.23  |
| N | 12.84  | 13.04 |

EXAMPLE II

This Example illustrates the reduction of the oxime intermediate from Example I.

A solution of 50 g (0.23 mol) of the oxime from Example I in 400 ml of tetrahydrofuran (THF, dried by distillation from $LiAlH_4$, followed by storage of the solvent over 3A molecular sieves) was added dropwise (at a rate to maintain a brisk reflux) to a stirred suspension of 8.7 g (0.23 mol) of $LiAlH_4$ in 100 ml of dry THF. After the addition was complete, the reaction mixture was heated under reflux overnight. The reaction mixture was then chilled in an ice-water bath and quenched, to liberate the basic product, with successive additions of 8.7 ml of $H_2O$, 8.7 ml of 15% sodium hydroxide, and 26.1 ml of $H_2O$. The insoluble material was removed by filtration, the solids washed with THF (3×200 ml), and the combined filtrates concentrated under vacuum. The residual oil was dissolved in methylene chloride (300 ml), washed with water (2×100 ml), dried over sodium sulfate and concentrated under vacuum. Vacuum distillation of the crude oily residue yielded a colorless product [35 g, 74%, bp. 142° C. (0.10 mm Hg)]. The product was placed in a storage container which was tightly capped and placed in a desiccator to protect the strongly basic amine from forming salts with atmospheric carbon dioxide ($H_2CO_3$). An analytically pure sample was obtained as the 1-(2-phenylethyl)-4-piperidineamine dihydrogen oxalate hemihydrate after recrystallization of the material from i-propanol-$H_2O$ (mp. 191°–192° C.).

|   | Calcd. | Found |
|---|--------|-------|
| C | 51.90  | 51.58 |
| H | 6.41   | 6.21  |

|   | Calcd. | Found |
|---|---|---|
| N | 7.12 | 7.11 |

EXAMPLE III

This Example illustrates alkylation of the intermediate from Example II.

A mixture of 12.5 g (75 mmol) of 2-chloropyridine N-oxide hydrochloride (Aldrich), 17 g (83 mmol) of the intermediate from Example II, 40 g of anhydrous sodium carbonate, 200 mg of potassium iodide, and 210 ml of 3-methyl-1-butanol was heated under reflux with stirring for 48 hours and then cooled and filtered. The filtrate was concentrated under vacuum. The residue was partitioned between 10% hydrochloric acid solution (200 ml) and ether (200 ml). The acidic aqueous phase was neutralized with 12N sodium hydroxide and the liberated free base was extracted with methylene chloride (2×200 ml). The organic extract was washed with water (200 ml), brine (100 ml), and then dried over sodium sulfate. Concentration of the solution under vacuum yielded a brown solid which was purified by chromatography (1000 g of fine silica; $CHCl_3$—$CH_3OH$—$NH_4OH$; 25:1:0.1) to yield 1-(2-phenylethyl)-4-[N-(1-oxo-2-aminopyridine)]piperidine as a light tan solid (9 g, 40%) which was homogeneous by TLC ($R_f$ 0.31; $CHCl_3$—$CH_3OH$—$NH_4OH$; 95:5:0:5).

EXAMPLE IV

This Example illustrates reduction of the intermediate from Example III.

Phosphorous trichloride (14 ml) was added dropwise to an ice-chilled solution of 4.6 g (16 mmol) of the intermediate from Example III in chloroform (100 ml), maintaining the internal temperature of the solution at about 0° C. The reaction mixture was then heated and stirred under reflux for 2 hours, cooled, and poured into ice. The acidic mixture was neutralized with aqueous 20% sodium hydroxide solution. The liberated free base was extracted with methylene chloride (2×100 ml) and the organic extract washed with water (200 ml), brine (200 ml), and dried over sodium sulfate. Concentration of the solution under vacuum and initial purification of the residue by flash chromatography (125 g fine silica; $CHCl_3$—$CH_3OH$—$NH_4OH$; 25:1:0.1) yielded a tan solid, which after further chromatography, yielded the product 1-(2-phenylethyl)-4-[N-(2-aminopyridine)]piperidine as an off-white solid (3 g, 61%).

EXAMPLE V

This Example illustrates acylation and conversion of the intermediate from Example IV to a compound according to the present invention.

A solution of 0.72 g of 2,5-dimethyl-3-furoyl chloride in 2 ml of dichloroethane was added to a stirred mixture of 1 g (3.6 mmol) of the intermediate from Example IV, 1 ml of triethylamine, and 8 ml of chloroform. The mixture was stirred at ambient temperature overnight at which time TLC analysis ($CHCl_3$—$CH_3OH$—$NH_4OH$; 95:5:0.5) of the mixture showed that the starting material was consumed. The reaction mixture was concentrated under vacuum and the residue partitioned between an aqueous solution of 10% hydrochloric acid (50 ml) and ether (50 ml). The aqueous phases was further extracted with ether and then the aqueous phases were combined and neutralized with 12N sodium hydroxide. The liberated free base was extracted with methylene chloride (2×50 ml) and the organic extract washed with water (50 ml), brine (50 ml), dried over sodium sulfate and concentrated under vacuum. Purification of the residue by flash chromatography (150 g fine silica; $CHCl_3$—$CH_3OH$—$NH_4OH$; 40:1:0.1) gave N-(2-pyridinyl)-N-[1-(2-phenylethyl)-4-piperdinyl]-2,5-dimethyl-3-furanamide as a desert tan solid (1.3 g, 89%). This solid was mixed and dissolved with 290 mg of oxalic acid in hot isopropyl alcohol. A few drops of isopropyl ether induced the precipitation of 1.145 g of N-(2-pyridinyl)-N-[1-(2-phenylethyl)-4-piperdinyl]-2,5-dimethyl-3-furanamide oxalate as a tan powder (mp. 196°-197° C.).

|   | Calcd. | Found |
|---|---|---|
| C | 65.71 | 65.43 |
| H | 6.33 | 6.35 |
| N | 8.51 | 8.36 |

EXAMPLE VI

This Example illustrates the preparation of an intermediate compound.

A mixture of 12.1 g (64 mmol) of 1-(phenylmethyl)-4-piperidineamine, prepared essentially according to the procedure described for the intermediate from Example II, 3.6 g (32 mmol) of chloropyrazine, and 2.0 g (32 mmol) of copper powder was stirred at 170°-180° C. for 6 hours. After being cooled, the green mixture solidified. The solid was broken into chunks and gradually churned into a thick soup in an aqueous solution of 10% hydrochloric acid (100 ml). The insolubles in the suspension were removed by filtration and the filtrate was extracted with ether (50 ml). Neutralization of the aqueous solution with 12N sodium hydroxide liberated the free base which was extracted with methylene chloride (2×50 ml). The organic extract was washed with water (50 ml), brine (50 ml), and dried over sodium sulfate. Concentration of the solution yielded a solid which was purified by chromatography (600 g of fine silica; $CHCl_3$—$CH_3OH$—$NH_4OH$; 4000 ml of 100:1:0.1, 1800 ml of 90:1:0.1, 1600 ml of 80:1:0.1, and 4000 ml of 70:1:0.1) to yield 3.7 g (44%) of 1-(phenylmethyl)-4-[N-(2-aminopyrazinyl)]piperidine as a beige solid.

EXAMPLE VII

This Example illustrates acylation of the intermediate from Example VI.

A quantity of 0.63 ml (6.4 mmol) of 2-furoyl chloride in 2 ml of chloroform was added to a stirred mixture of the intermediate from Example VI (1.4 g, 5.3 mmol) in 1.5 ml of triethylamine and 13 ml of chloroform. This solution was stirred under reflux for 5 hours, then cooled and concentrated under vacuum. The mixture was partitioned between an aqueous solution of 10% hydrochloric acid (50 ml) and ether (50 ml). The aqueous phase was neutralized with 12N sodium hydroxide and extracted with methylene chloride (2×50 ml). The organic extract was washed with water (50 ml), brine (30 ml), dried over sodium sulfate and concentrated under vacuum. Purification of the residue by flash chromatography (55 g fine silica; $CHCl_3$—$CH_3OH$—$NH_4OH$, 30:1:0.1) gave N-(2-pyrazinyl)-N-(1-phenylmethyl-4-piperidinyl)-2-furanamide as a white solid (0.85 g, 45%). The hydrogen oxalate salt of the free base was prepared by recrystallization of the intermediate from isopropyl alcohol solution to yield 650 mg of a crude powder.

EXAMPLE VIII

This Example illustrates cleavage of the phenymethyl group (debenzylation) in the intermediate from Example VII.

A solution of 1-chloroethyl chloroformate (9.7 ml, 90 mmol) in 1,2-dichloroethane (25 ml) was added to an ice-chilled solution of N-(2-pyrazinyl)-N-(1-phenylmethyl-4-piperidinyl)-2-furanamide (45 mmol) and 1,2-dichloroethane (125 ml). The reaction mixture was stirred under reflux for 5 hours, then cooled and concentrated under vacuum. The crude carbamate residue was dissolved in methanol (150 ml) and the reaction solution was heated under reflux for 2 hours. The reaction solution was cooled, decolorizing carbon (10 g, Darco G-60) was added to the mixture, then the suspension was heated and stirred under reflux for 15 minutes. The suspension was filtered through Celite and the filtrate was concentrated under vacuum. The residue was suspended in hot isopropanol (100 ml), then cooled and filtered. The pale maize colored powder was dried under vacuum (85° C., 0.01 mm Hg, 2 hours) to yield N-(2-pyrazinyl)-N-(4-piperidinyl)-2-furanamide (8.9 g, 72%) as the hydrochloride salt.

EXAMPLE IX

This Example illustrates N-alkylation of the intermediate from Example VIII to form a compound according to the present invention.

A mixture of the hydrochloride salt of the intermediate from Example VIII (14 mmol), 2-(2-chloroethyl)thiophene (70 mmol), anhydrous sodium bicarbonate (5 g), anhydrous sodium iodide (0.7 g) and acetonitrile (50 ml) was heated under reflux overnight, at which time TLC analysis (CHCl$_3$—CH$_3$OH—NH$_4$OH; 95:5:0.5) of the mixture showed consumption of the starting material. The suspension was cooled and filtered and the filtrate was concentrated under vacuum. The residue was partitioned between an aqueous solution of 10% hydrochloric acid (50 ml) and ether (50 ml). The acidic aqueous phase was neutralized with 12N sodium hydroxide and extracted with methylene chloride (2×50 ml). The organic extract was washed with water (50 ml), brine (30 ml), dried over sodium sulfate and concentrated under vacuum. Purification of the residue (1.8 g) by column chromatography (400 g fine silica; CHCl$_3$—CH$_3$OH—NH$_4$OH, 50:1:0.1) gave the product N-(2-pyrazinyl)-N-(1-(2-(2-thienyl)ethyl)-4-piperidinyl)-2-furanamide as a caramel gum (1.1 g, 21%). The hydrogen oxalate salt of the free base was prepared by recrystallization of the product from isopropyl alcohol solution to yield 650 mg of a tan powder (mp. 211.5°–213.5° C.).

|   | Calcd. | Found |
|---|---|---|
| C | 55.92 | 55.80 |
| H | 5.12 | 5.18 |
| N | 11.86 | 11.86 |
| S | 6.78 | 6.79 |

EXAMPLES X-L

Further examples of compounds within the scope of the present invention which may be prepared by procedures analogous to those described above include:

N-(2-pyrimidinyl)-N-[1-(2-phenylethyl)-4-piperidinyl]-2,5-dimethyl-3-furanamide

N-(2-pyrimidinyl)-N-[1-(2-phenylethyl)-4-piperidinyl]-2-thienamide

N-(2-pyrimidinyl)-N-[1-(2-phenylethyl)-4-piperidinyl]-3-thienamide

N-(2-pyridinyl)-N-[1-(2-phenylethyl)-4-piperidinyl]-1-methyl-2-pyrrolamide

N-(2-pyridinyl)-N-[1-(2-phenylethyl)-4-piperidinyl]-3-thienamide

N-(2-pyridinyl)-N-[1-(2-phenylethyl)-4-piperidinyl]-2,5-dimethyl-3-furanamide

N-(2-pyridinyl)-N-[1-(2-phenylethyl)-4-piperidinyl]-3-thienamide

N-(2-chloro-3-pyridinyl)-N-[1-(2-phenylethyl)-4-piperidinyl]-2-thienamide

N-(2-methyl-6-pyridinyl)-N-[1-(2-phenylethyl)-4-piperidinyl]-2-thienamide

N-(4-methyl-2-pyridinyl)-N-[1-(2-(3-thienyl)ethyl)-4-piperidinyl]-2-furanamide

N-(4-methyl-2-pyridinyl)-N-[1-(2-(1-pyrazoyl)ethyl)-4-piperidinyl]-2-furanamide

N-(4-methyl-2-pyridinyl)-N-[1-(2-(4-ethyl-4,5-dihydro-5-oxo-1H-tetrazol-1-yl)ethyl)-4-piperidinyl]-2-furanamide N-(2-pyridinyl)-N-[1-(2-(1-pyrazolyl)ethyl)-4-piperidinyl]cyclopropanamide N-(2-pyrazinyl)-N-[1-(1-(methyl-2-hydroxy-2-(2-thienyl)ethyl)-4-piperidinyl]-2-furanamide N-(2-pyrazinyl)-N-[1-(2-(1-pyrazolyl)ethyl)-4-piperidinyl]-2-furanamide N-(2-pyrazinyl)-N-[1-(2-hydroxy-2-(2-thienyl)ethyl)-4-piperidinyl]-2-furanamide N-(2-pyrazinyl)-N-[1-(2-(3-thienyl)ethyl)-4-piperidinyl]-2-furanamide cis-N-(2-pyridinyl)-N-[1-(2-phenylethyl)-3-methyl-4-piperidinyl]-2-furanamide cis-N-(2-pyridinyl)-N-[1-(2-phenylethyl)-3-methyl-4-piperidinyl]cyclopropanamide cis-N-(2-pyridinyl)-N-[1-(2-phenylethyl)-3-methyl-4-piperidinyl]methoxyacetamide cis-N-(2-pyridinyl)-N-[1-(2-phenylethyl)-3-methyl-4-piperidinyl]-3-furanamide cis-N-(2-pyridinyl)-N-[1-(2-phenylethyl)-3-methyl-4-piperidinyl]-3-thienamide cis-N-(2-pyridinyl)-N-[1-(2-phenylethyl)-3-methyl-4-piperidinyl]-2-bromo-5-furanamide trans-N-(2-pyridinyl)-N-[1-(2-phenylethyl)-3-methyl-4-piperidinyl]-2-thienamide trans-N-(2-pyridinyl)-N-[1-(2-phenylethyl)-3-methyl-4-piperidinyl]-2,5-dimethyl-3-furanamide trans-N-(2-pyridinyl)-N-[1-(2-phenylethyl)-3-methyl-4-piperidinyl]-3-thienamide cis-N-(4-methyl-2-pyridinyl)-N-[1-(2-phenylethyl)-3-methyl-4-piperidinyl]-2-furanamide cis-N-(4-methyl-2-pyridinyl)-N-[1-(2-phenylethyl)-3-methyl-4-piperidinyl]-2-thienamide cis-N-(2-pyrazinyl)-N-[1-(2-phenylmethyl)-3-methyl-4-piperidinyl]-2-furanamide cis-N-(2-pyrazinyl)-N-[1-(2-phenylethyl)-3-methyl-4-piperidinyl]-2-furanamide cis-N-(2-pyrazinyl)-N-[1-(2-phenylethyl)-3-methyl-4-piperidinyl]-2-thienamide trans-N-(2-pyrazinyl)-N-[1-(2-phenylethyl)-3-methyl-4-piperidinyl]-2-furanamide trans-N-(2-pyrazinyl)-N-[1-(2-phenylethyl)-3-methyl-4-piperidinyl]-2-thienamide cis-N-(2-pyrimidinyl)-N-[1-(2-phenylethyl)-3-methyl-4-piperidinyl]-2-furanamide
cis-N-(2-pyrimidinyl)-N-[1-(2-phenylethyl)-3-methyl-4-piperidinyl]cyclopropanamide
cis-N-(2-pyrimidinyl)-N-[1-(2-phenylethyl)-3-methyl-4-piperidinyl]-3-thienamide
cis-N-(2-pyrimidinyl)-N-[1-(2-phenylethyl)-3-methyl-4-piperidinyl]methoxyacetamide
trans-N-(2-pyrimidinyl)-N-[1-(2-phenylethyl)-3-methyl-4-piperidinyl]-2,5-dimethyl-3-furanamide
trans-N-(2-pyrimidinyl)-N-[1-(2-phenylethyl)-3-methyl-4-piperidinyl]-3-thienamide
cis-N-(4-methyl-2-pyridinyl)-N-[1-(2-(1-pyrazolyl)ethyl)-3-methyl-4-piperidinyl]-2-furanamide
cis-N-(4-methyl-2-pyridinyl)-N-[1-(2-(4-ethyl-4,5-dihydro-5-oxo-1H-tetrazol-1-yl)ethyl)-3-methyl-4-piperidinyl]-2-furanamide

EXAMPLE LI

A pharmaceutical composition for parental or intravenous analgesic administration can be prepared from the following ingredients:

| COMPONENTS | AMOUNTS |
| --- | --- |
| N—(2-pyridinyl)-N—[1-(2-phenylethyl)-4-piperidinyl]-2,5-dimethyl-3-furanamide | 1 mg |
| isotonic water | 10 liters |

Of course, other compounds of this invention such as those set out in Examples X–L may be substituted for N-(2-pyridinyl)-N-[1-(2-phenylethyl)-4-piperidinyl]-2,5-dimethyl-3-furanamide with the relative amount of such other compounds in the compositions depending upon their analgesic activity.

EXAMPLE LII

A number of compounds in accordance with the present invention were tested for their analgesic (agonist and antagonist) properties. Specifically, the acid addition salts of the compounds, tested in accordance with the invention, were dissolved in sterile water for injection, USP, to form a solution, the concentration of which may vary from 0.00001 mg/ml to 5 mg/ml. The solution was administered intravenously into a mouse tail vain. The $ED_{50}$ values were obtained from the mouse hot plate analgesia test (58° C.) as described in Domer, Floyd R., *Animal Experiments in Pharmacological Analysis*, Charles C. Thomas, Springfield, 1971, p. 283 ff. The compounds listed in Tables 1 and 2 were tested by this procedure and found to have the activities listed in the columns on the right side of Tables 1 and 2.

The reversal characteristics of the inventive compounds were investigated with respect to morphine in rabbits and categorized by an integer such as 0, 1, or 2. The number 0 means no reversal of morphine effects, the number 1 means reversal of only morphine respiratory depression, and the number 2 means reversal of both respiratory depression and analgesia. The symbol NA means the compound was not active as an anesthetic or analgesic at less than 10 mg/kg.

TABLE 1

| COMPOUNDS | M.P. °C. | ANALGESIC ACTIVITY $ED_{50}$ MG/KG | REVERSAL CHARACTERISTICS |
| --- | --- | --- | --- |
| 1. N—(2-pyrimidinyl)-N—[1-(2-phenylethyl)-4-piperidinyl]-2,5-dimethyl-3-furanamide | 203–204 | >1 | ND |
| 2. N—(2-pyrimidinyl)-N—[1-(2-phenylethyl)-4-piperidinyl]-2-thienamide | 209–210 | 0.806 | ND |
| 3. N—(2-pyrimidinyl)-N—[1-(2-phenylethyl)-4-piperidinyl]-3-thienamide | 214 | 0.71 | ND |
| 4. N—(2-pyridinyl)-N—[1-(2-phenylethyl)-4-piperidinyl]-1-methyl-2-pyrrolamide | 206–207 | NA | ND |
| 5. N—(2-pyridinyl)-N—[1-(2-phenylethyl)-4-piperidinyl]-3-thienamide | 229–230 | 1.45 | ND |
| 6. N—(2-pyridinyl)-N—[1-(2-phenylethyl)-4-piperidinyl]-2,5-dimethyl-3-furanamide | 196–197 | 3.2 | ND |
| 7. N—(3-pyridinyl-N—[1-(2-phenylethyl)-4-piperidinyl]-2,5-dimethyl-3-furanamide | 15–152 | <1 | ND |
| 8. N—(3-pyridinyl)-N—[1-(2-phenylethyl)-4-piperidinyl]-3-thienamide | 190–192 | 1.2 | ND |
| 9. N—(2-chloro-3-pyridinyl)-N—[1-(2-phenylethyl)-4-piperidinyl]-2-thienamide | 181.5–182.5 | 0.015 | ND |
| 10. N—(2-methyl-6-pyridinyl)-N—[1-(2-phenylethyl)-4-piperidinyl]-2-thienamide | 200–201 | 3.8 | ND |
| 11. N—(4-methyl-2-pyridinyl)-N—[1-(2-(3-thienyl)ethyl)-4-piperidinyl]-2-furanamide | 194–195 | >1 | 2 |
| 12. N—(4-methyl-2-pyridinyl)-N—[1-(2-(1-pyrazoyl)ethyl)-4-piperidinyl]-2-furanamide | 172–173.5 | NA | ND |
| 13. N—(4-methyl-2-pyridinyl)-N—[1-(2-(4-ethyl-4,5-dihydro-5-oxo-1H—tetrazol-1-yl)ethyl)-4-piperidinyl]-2-furanamide | 171.5–172 | NA | 0 |
| 14. N—(2-pyridinyl)-N—[1-(2-(1-pyrazolyl)ethyl)-4-piperidinyl]cyclopropanamide | 196–197 | 2.98 | ND |
| 15. N—(2-pyrazinyl)-N—[1-(2-(2-thienyl)ethyl)-4-piperidinyl]-2-furanamide | 213–217 | <1 | 2 |
| 16. N—(2-pyrazinyl)-N—[1-(1-methyl-2-hydroxy-2-(2-thienyl)ethyl)-4-piperidinyl]-2-furanamide | 170 | >5 | 2 |
| 17. N—(2-pyrazinyl)-N—[1-(2-(1-pyrazolyl)ethyl)-4-piperidinyl]-2-furanamide | 214–215.5 | NA | 1 |
| 18. N—(2-pyrazinyl)-N—[1-(2-hydroxy-2-(2-thienyl)ethyl)-4-piperidinyl]-2-furanamide | 215 | >5 | ND |
| 19. N—(2-pyrazinyl)-N—[1-(2-(3-thienyl)ethyl)- | 220 | 3.0 | ND |

TABLE 1-continued

| COMPOUNDS | M.P. °C. | ANALGESIC ACTIVITY ED$_{50}$ MG/KG | REVERSAL CHARACTERISTICS |
|---|---|---|---|
| 4-piperidinyl]-2-furanamide | | | |

NA = Not Available
ND = Not Determined

TABLE 2

| COMPOUNDS | M.P. °C. | ANALGESIC ACTIVITY ED$_{50}$ MG/KG | REVERSAL CHARACTERISTICS |
|---|---|---|---|
| 1. cis-N—(2-pyridinyl)-N—[1-(2-phenylethyl)-3-methyl-4-piperidinyl]-2-furanamide | 189–190 | 0.016 | ND |
| 2. cis-N—(2-pyridinyl)-N—[1-(2-phenylethyl)-3-methyl-4-piperidinyl]cyclopropanamide | 151–153 | 0.0016 | ND |
| 3. cis-N—(2-pyridinyl)-N—[1-(2-phenylethyl)-3-methyl-4-piperidinyl]methoxyacetamide | 156.5–157 | 0.0014 | ND |
| 4. cis-N—(2-pyridinyl)-N—[1-(2-phenylethyl)-3-methyl-4-piperidinyl]-3-furanamide | 179.5–183 | 0.0087 | ND |
| 5. cis-N—(2-pyridinyl)-N—[1-(2-phenylethyl)-3-methyl-4-piperidinyl]-3-thienamide | 186.5–188 | 0.012 | ND |
| 6. cis-N—(2-pyridinyl)-N—[1-(2-phenylethyl)-3-methyl-4-piperidinyl]-2-bromo-5-furanamide | 174–175 | 0.597 | ND |
| 7. trans-N—(2-pyridinyl)-N—[1-(2-phenylethyl)-3-methyl-4-piperidinyl]-2-thienamide | 175–177 | 0.258 | ND |
| 8. trans-N—(2-pyridinyl)-N—[1-(2-phenylethyl)-3-methyl-4-piperidinyl]-2,5-dimethyl-3-furanamide | 179–180 | >1 | ND |
| 9. trans-N—(2-pyridinyl)-N—[1-(2-phenylethyl)-3-methyl-4-piperidinyl]-3-thienamide | 186–187 | 0.602 | ND |
| 10. cis-N—(4-methyl-2-pyridinyl)-N—[1-(2-phenylethyl)-3-methyl-4-piperidinyl]-2-furanamide | 182–183 | 0.011 | ND |
| 11. cis-N—(4-methyl-2-pyridinyl)-N—[1-(2-phenylethyl)-3-methyl-4-piperidinyl]-2-thienamide | 175 | 0.166 | ND |
| 12. cis-N—(2-pyrazinyl)-N—[1-(2-phenylmethyl)-3-methyl-4-piperidinyl]-2-furanamide | 182–183.5 | 2.5 | ND |
| 13. cis-N—(2-pyrazinyl)-N—[1-(2-phenylethyl)-3-methyl-4-piperidinyl]-2-furanamide | 205.5–207 | 0.0098 | ND |
| 14. cis-N—(2-pyrazinyl)-N—[1-(2-phenylethyl)-3-methyl-4-piperidinyl]-2-thienamide | 211–211.5 | 0.0175 | ND |
| 15. trans-N—(2-pyrazinyl)-N—[1-(2-phenylethyl)-3-methyl-4-piperidinyl]-2-furanamide | 198–199 | >1 | ND |
| 16. trans-N—(2-pyrazinyl)-N—[1-(2-phenylethyl)-3-methyl-4-piperidinyl]-2-thienamide | 196–196.5 | 0.61 | ND |
| 17. cis-N—(2-pyrimidinyl)-N—[1-(2-phenylethyl)-3-methyl-4-piperidinyl]-2-furanamide | 144–145 | 0.009 | ND |
| 18. cis-N—(2-pyrimidinyl)-N—[1-(2-phenylethyl)-3-methyl-4-piperidinyl]cyclopropanamide | 184.5–185.5 | 0.0015 | ND |
| 19. cis-N—(2-pyrimidinyl)-N—[1-(2-phenylethyl)-3-methyl-4-piperidinyl]-3-thienamide | 184–186.5 | 0.009 | ND |
| 20. cis-N—(2-pyrimidinyl)-N—[1-(2-phenylethyl)-3-methyl-4-piperidinyl]methoxyacetamide | 137–139.5 | 0.0048 | ND |
| 21. trans-N—(2-pyrimidinyl)-N—[1-(2-phenylethyl)-3-methyl-4-piperidinyl]-2,5-dimethyl-3-furanamide | 184–185 | 0.736 | ND |
| 22. trans-N—(2-pyrimidinyl)-N—[1-(2-phenylethyl)-3-methyl-4-piperidinyl]-3-thienamide | 207–209.5 | 0.155 | ND |
| 23. cis-N—(4-methyl-2-pyridinyl)-N—[1-(2-(1-pyrazolyl)ethyl)-3-methyl-4-piperidinyl]-2-furanamide | 189–193 | 0.279 | ND |
| 24. cis-N—(4-methyl-2-pyridinyl)-N—[1-(2-(4-ethyl-4,5-dihydro-5-oxo-1H—tetrazol-1-yl)ethyl)-3-methyl-4-piperidinyl]-2-furanamide | 151 | 2.3 | ND |

ND = Not Determined

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:
1. A compound having the formula:

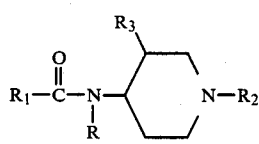

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower- alkylthio, oxygen, and combinations thereof;

R₁ is selected from the group consisting of furanyl lower-alkyl, thienyl lower-alkyl, pyrrolyl, pyrrolyl lower-alkyl, and lower-alkyl and lower-cycloalkyl of 2 to 6 carbons, wherein the R₁ groups may be either unsubstituted or substituted with the substituents independently selected from the group consisting of halogen, lower-alkyl, lower-alkoxy, halogenated lower-alkyl, lower-alkylthio, oxygen, and combinations thereof;

R₂ is selected from the group consisting of thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the R₂ group may be either unsubstituted or substituted with the substituents indepently selected from the group consisting of halogen, lower-alkyl, lower-alkoxy, halogenated lower-alkyl, lower-alkylthio, oxygen, and combinations thereof; and R₃ is hydrogen.

2. The compound according to claim 1, which comprises N-(2-pyrazinyl)-N-[1-(2-(2-thienyl)ethyl)-4-piperidinyl]-2-furanamide and the pharmaceutically acceptable acid addition salts thereof.

3. The compound according to claim 1, which comprises N-(2-pyrazinyl)-N-[1-(2-(1-pyrazolyl)ethyl)-4-piperidinyl]-2-furanamide and the pharmaceutically acceptable acid addition salts thereof.

4. The compound according to claim 1, which comprises N-(2-pyrazinyl)-N-[1-(2-(3-thienyl)ethyl)-4-piperidinyl]-2-furanamide and the pharmaceutically acceptable acid addition salts thereof.

5. A compound having the formula:

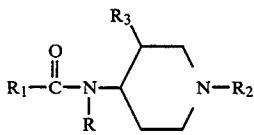

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower- alkylthio, oxygen, and combinations thereof;

R₁ is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons, wherein the R₁ groups may be either unsubstituted or substituted with the substituents independently selected from the group consisting of halogen, lower-alkyl, lower-alkoxy, halogenated lower-alkyl, lower-alkylthio, oxygen, and combinations thereof;

R₂ is selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the R₂ group may be either unsubstituted or substituted with the substituents independently selected from the group consisting of halogen, lower-alkyl, lower-alkoxy, halogenated lower-alkyl, lower-alkylthio, oxygen, and combinations thereof;

and R₃ is methyl.

6. The compound according to claim 5, which comprises cis-N-(2-pyrazinyl)-N-[1-(2-phenylethyl)-3-methyl-4-piperidinyl]-2-furanamide and the pharmaceutically acceptable acid addition salts thereof.

7. The compound according to claim 5, which comprises trans-N-(2-pyrazinyl)-N-[1-(2-phenylethyl)-3-methyl-4-piperidinyl]-2-thienamide and the pharmaceutically acceptable acid addition salts thereof.

8. A narcotic antagonistic or analgesic composition comprising a non-toxic pharmaceutically acceptable carrier and an analgesically or antagonistically effective amount of a compound having the formula:

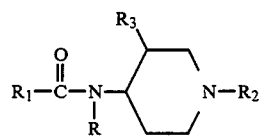

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower-alkylthio, oxygen, and combinations thereof;

R₁ is selected from the group consisting of furanyl lower-alkyl, thienyl lower-alkyl, pyrrolyl, pyrrolyl lower-alkyl, and lower-alkyl and lower-cycloalkyl of 2 to 6 carbons, wherein the R₁ groups may be either unsubstituted or substituted with the substituents independently selected from the group consisting of halogen, lower-alkyl, lower-alkoxy, halogenated lower-alkyl, lower-alkylthio, oxygen, and combinations thereof;

R₂ is selected from the group consisting of thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the R₂ group may be either unsubstituted or substituted with the substituents independently selected from the group consisting of halogen, lower-alkyl, lower-alkoxy, halogenated lower-alkyl, lower-alkylthio, oxygen, and combinations thereof; and R₃ is hydrogen.

9. The composition according to claim 8, wherein the compound comprises N-(2-pyrazinyl)-N-[1-(2-(2-thienyl)ethyl)-4-piperidinyl]-2-furanamide and the pharmaceutically acceptable acid addition salts thereof.

10. The composition according to claim 8, wherein the compound comprises N-(2-pyrazinyl)-N-[1-(2-(1-pyrazolyl)ethyl)-4-piperidinyl]-2-furanamide and the pharmaceutically acceptable acid addition salts thereof.

11. The composition according to claim 8, wherein the compound comprises N-(2-pyrazinyl)-N-[1-(2-(3-thienyl)ethyl)-4-piperidinyl]-2-furanamide and the pharmaceutically acceptable acid addition salts thereof.

12. A narcotic antagonistic or analgesic composition comprising a non-toxic pharmaceutically acceptable carrier and an analgesically or antagonistically effective amount of a compound having the formula:

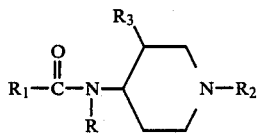

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower-alkylthio, oxygen, and combinations thereof;

$R_1$ is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons, wherein the $R_1$ groups may be either unsubstituted or substituted with the substituents independently selected from the group consisting of halogen, lower-alkyl, lower-alkoxy, halogenated lower-alkyl, lower-alkylthio, oxygen, and combinations thereof;

$R_2$ is selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the $R_2$ group may be either unsubstituted or substituted with the substituents independently selected from the group consisting of halogen, lower-alkyl, lower-alkoxy, halogenated lower-alkyl, lower-alkylthio, oxygen, and combinations thereof; and $R_3$ is methyl.

13. The composition according to claim 12, wherein the compound comprises cis-N-(2-pyrazinyl)-N-[1-(2-phenylethyl)-3-methyl-4-piperidinyl]-2-furanamide and the pharmaceutically acceptable acid addition salts thereof.

14. The composition according to claim 12, wherein the compound comprises trans-N-(2-pyrazinyl)-N-[1-(2-phenylethyl)-3-methyl-4-piperidinyl]-2-thienamide and the pharmaceutically acceptable acid addition salts thereof.

15. A method for producing analgesia or selectively reversing the actions of opiate analgesics in a mammal, including respiratory depression, comprising administering to the mammal an analgesically or antagonistically effective amount of a compound having the formula:

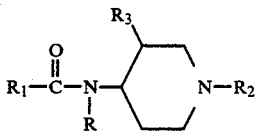

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower-alkylthio, oxygen, and combinations thereof;

$R_1$ is selected from the group consisting of furanyl lower-alkyl, thienyl lower-alkyl, pyrrolyl, pyrrolyl lower-alkyl, and lower-alkyl and lower-cycloalkyl of 2 to 6 carbons, wherein the $R_1$ groups may be either unsubstituted or substituted with the substituents independently selected from the group consisting of halogen, lower-alkyl, lower-alkoxy, halogenated lower-alkyl, lower-alkylthio, oxygen, and combinations thereof;

$R_2$ is selected from the group consisting of thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the $R_2$ group may be either unsubstituted or substituted with the substituents independently selected from the group consisting of halogen, lower-alkyl, lower-alkoxy, halogenated lower-alkyl, lower-alkylthio, oxygen, and combinations thereof; and $R_3$ is hydrogen.

16. The method according to claim 15 wherein the compound comprises N-(2-pyrazinyl)-N-[1-(2-(2-thienyl)ethyl)-4-piperidinyl]-2-furanamide and the pharmaceutically acceptable acid addition salts thereof.

17. The method according to claim 15 wherein the compound comprises N-(2-pyrazinyl)-N-[1-(2-(1-pyrazolyl)ethyl)-4-piperidinyl]-2-furanamide and the pharmaceutically acceptable acid addition salts thereof.

18. The method according to claim 15 wherein the compound comprises N-(2-pyrazinyl)-N-[1-(2-(3-thienyl)ethyl)-4-piperidinyl]-2-furanamide and the pharmaceutically acceptable acid addition salts thereof.

19. A method for producing analgesia or selectively reversing the actions of opiate analgesics in a mammal, including respiratory depression, comprising administering to the mammal an analgesically or antagonistically effective amount of a compound having the formula:

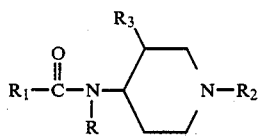

and the optically active isomeric forms, and the pharmaceutically acceptable acid addition salts thereof, in which formula:

R is a pyrazinyl group which may be unsubstituted or substituted with substituents independently selected from the group consisting of halogen, lower-alkyl, lower-alkoxy, halogenated lower-alkyl, lower-alkylthio, oxygen, and combinations thereof;

$R_1$ is selected from the group consisting of furanyl, furanyl lower-alkyl, thienyl, thienyl lower-alkyl, pyrrolyl, pyrrolyl lower-alkyl, lower-alkyl, lower-cycloalkyl, and lower-alkoxy lower-alkyl of 2 to 6 carbons, wherein the R1 groups may be either unsubstituted or substituted with the substituents independently selected from the group consisting of halogen, lower-alkyl, lower-alkoxy, halogenated lower-alkyl lower-alkylthio, oxygen, and combinations thereof;

$R_2$ is selected from the group consisting of phenyl lower-alkyl, thienyl lower-alkyl, thienyl hydroxy lower-alkyl, pyrazoyl lower-alkyl, and (4,5-dihydro-5-oxo-1H-tetrazol-1-yl) lower-alkyl, which may be substituted in the 4-position with a group selected from lower-alkyl, wherein the $R_2$ group may be either unsubstituted or substituted with the substituents independently selected from the group consisting of halogen, lower-alkyl, lower-alkoxy, halogenated lower-alkyl, lower-alkylthio, oxygen, and combinations thereof; and $R_3$ is methyl.

20. The method according to claim 19, wherein the compound comprises cis-N-(2-pyrazinyl)-N-[1-(2-phenylethyl)-3-methyl-4-piperidinyl]-2-furanamide and the pharmaceutically acceptable acid addition salts thereof.

21. The method according to claim 19, wherein the compound comprises trans-N-(2-pyrazinyl)-N-[1-(2-phenylethyl)-3-methyl-4-piperidinyl]-2-thienamide and the pharmaceutically acceptable acid addition salts thereof.

* * * * *